United States Patent [19]

Hoffman et al.

[11] Patent Number: 4,596,464
[45] Date of Patent: Jun. 24, 1986

[54] SCREENING METHOD FOR RED CELL ABNORMALITY

[75] Inventors: Robert A. Hoffman, Mansfield; Richard L. Kane, Norwood; Brandon J. Price, Norfolk; Russell J. Gershman, Middleborough, all of Mass.

[73] Assignee: Ortho Diagnostic Systems, Inc., Raritan, N.J.

[21] Appl. No.: 557,689

[22] Filed: Dec. 2, 1983

Related U.S. Application Data

[63] Continuation-in-part of Ser. No. 542,221, Oct. 14, 1983.

[51] Int. Cl.⁴ ............................................. G01N 15/02
[52] U.S. Cl. ..................... 356/336; 356/39; 377/11; 364/555
[58] Field of Search .................. 356/335, 336, 39, 73, 356/317–319; 250/574, 461.2, 573, 575, 576; 377/10, 11, 12; 73/1 R; 364/416, 555; 324/71.4; 382/6

[56] References Cited

U.S. PATENT DOCUMENTS

| | | | |
|---|---|---|---|
| 3,686,486 | 8/1972 | Coulter et al. | 377/12 X |
| 4,021,117 | 5/1977 | Gohde et al. | 356/335 X |
| 4,086,631 | 4/1978 | Vick | 364/416 |
| 4,110,043 | 8/1978 | Eisert | 356/337 X |
| 4,251,733 | 2/1981 | Hirleman | 356/335 X |
| 4,263,508 | 4/1981 | Leary et al. | 356/335 X |
| 4,453,266 | 6/1984 | Bacus | 382/6 |

Primary Examiner—Vincent P. McGraw
Assistant Examiner—Robert D. V. Thompson, III
Attorney, Agent, or Firm—Audley A. Ciamporcero, Jr.

[57] ABSTRACT

Red cell samples are passed through a zone of focused illumination, and a scatter vs. time pulse is obtained for each. Each pulse is analyzed for pulse width, pulse area, and pulse shape. These parameters are respectively collected, and three coefficients of variation are obtained for each such collection. In addition to these three abnormality factors, the mean of the pulse shape collection constitutes a fourth. The four are respectively subject to statistical criteria, and are combined in predetermined fashion for a single red cell morphology index.

3 Claims, 6 Drawing Figures

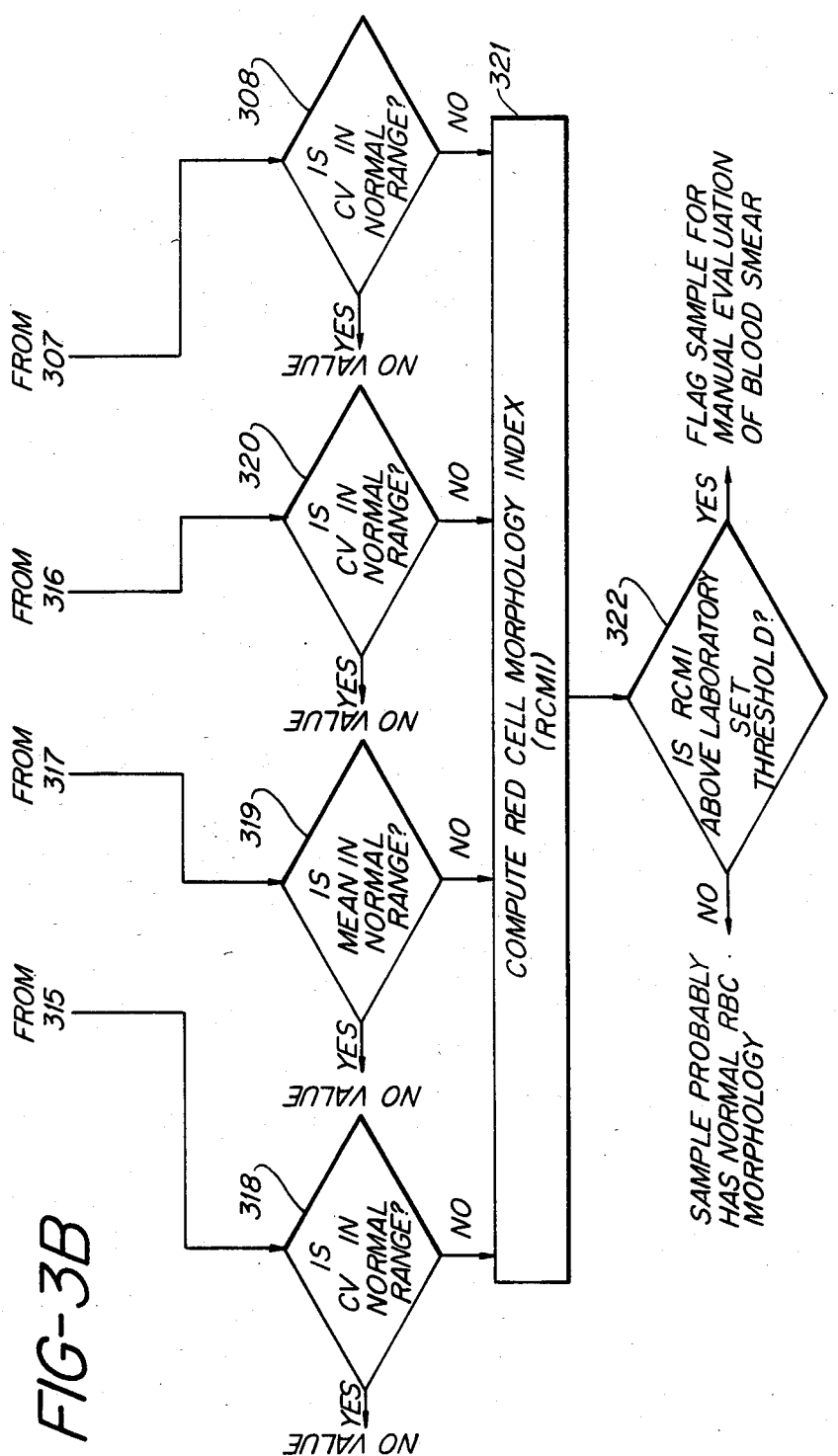

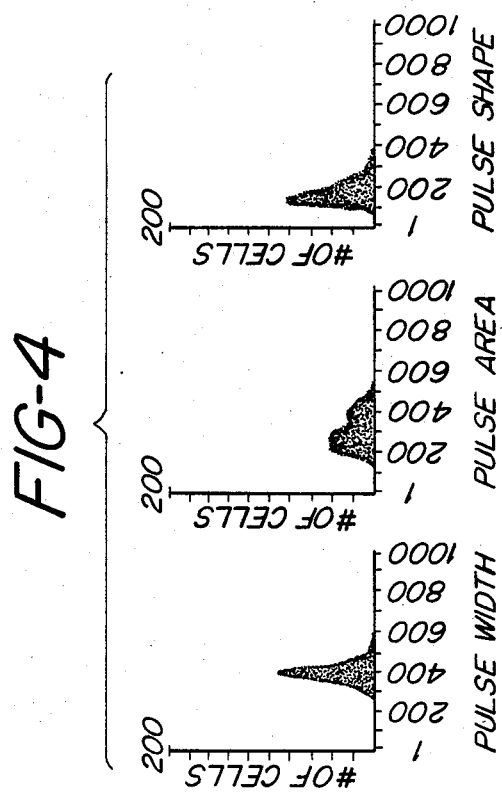

SCREENING METHOD FOR RED CELL ABNORMALITY

This is a continuation in part of U.S. Application Ser. No. 542,221, filed Oct. 14, 1983.

FIELD OF THE INVENTION

This invention relates to automated blood cell analysis, and more particularly to methods for automatically screening for abnormalities in red blood cells.

BACKGROUND OF THE INVENTION

Accurate sizing of red blood cells is an important measurement in the determination of various pathologic hematologic conditions. Normal red cell diameter is typically 7.5–8.3$\mu$. Iron deficiency anemias and thalassemias result in microcytosis, where red cell diameters may be as small as 6$\mu$. Megaloblastic anemias, pernicious anemia, and folate and vitamin $B_{12}$ deficiencies, on the other hand, lead to macrocytosis, where red cell diameters can be 9$\mu$ or larger. Price-Jones, in 1933, was the first to quantify, by direct microscopic measurement, variations in red blood cell sizes. The Price-Jones histogram of frequency of occurrence versus cell size has been used to relate these variations to differences in the physiology and pathology of stress and disease situations. Because these direct measurements are arduous and involve relatively small numbers of cells, this procedure has largely been ignored as a routine quantitative parameter by hematology laboratories. With the advent of electronic cell counters and analyzers, the mean corpuscular volume (MCV) has become the standard index for measuring the average size (volume) or thousands of cells in a matter of seconds. The problem with MCV, however, is that it only provides an average value and gives little information concerning the actual size and/or shape of individual cells.

It is, accordingly, a primary object of the present invention to provide faster, more accurate, and more reliable methods of investigating red blood cell abnormalities.

It is a related object to utilize the principles of optical flow cytometry to create a red cell abnormality screening vehicle.

Several investigators have reported using slit-width or time-of-flight ("TOF") measurements of impedance, light scatter, or fluorescence pulses generated by electronic cell counters to estimate cell size. These measurements are fairly accurate for spherical particles, but less advantageous for real cells which are of varying shapes and refractive indices. Leary, Todd, Wood and Jett, in 1979, increased the resolution over TOF analyses by looking at pulse risetime measurements, which they found to also be highly linear functions of diameter for microspheres. As a result of this work, James F. Leary and Paul Todd have a U.S. Pat. No. 4,263,508, issued on Apr. 21, 1981, entitled Pulse Edge Measurement for Determining Particle Dimensional Characteristics.

It is another object of the present invention to utilize the dynamics of cell counters, but more efficiently to rely on the wealth of information thereby made available. For example, it has been found that in the normal processing of samples in a commercially available clinical optical flow cytometry instrument (such as the one available from Ortho Diagnostic Systems Inc. of Raritan, NJ and Westwood, MA, the assignee hereof, under the trade name ELT-8) as many as thirty-three relevant parameters may be indexed. Clearly, it is desirable to base red cell abnormality investigations on an optimum selection of these parameters, considering the need for accuracy offset against the time and cost of complex processing.

SUMMARY OF THE INVENTION

The principles of the present invention are premised on the select utilization of narrow angle light scatter data and particularly of the parameters of pulse area, pulse width, and pulse shape. In particular, each cell is passed through a zone of focused illumination in conventional fashion, and narrow angle light scatter is noted for each. Thus, for each cell, there is produced a pulse (voltage proportional to light scatter, as a function of time) which corresponds to the cell causing the scatter. In accordance with the present invention, these pulses are measured individually, and the respective parameters are accumulated and analyzed. In turn, the results of the analysis are combined in select fashion to produce an index of red cell abnormality.

In a preferred embodiment, pulse shape is expressed as a ratio of pulse width (e.g., from 50% of peak on the rise to 50 of peak on the fall) to peak, and collections of these pulse shape characteristics are analyzed selectively for coefficient of variation and mean. These two, together with coefficients of variation of the pulse area and pulse width collections, represent separate factors conveying varying amounts of information regarding abnormality.

In order to assemble a definitive index, each must be separately weighted, and then combined. More specific aspects of the present invention, detailed hereinafter, provide bases for this separate weighting and combination functions.

DESCRIPTION OF THE DRAWINGS

FIGS. 3A and 3B, jointly hereinafter referred to as FIG. 3, show in flow chart form a preferred method in accordance with the principles of the present invention;

FIG. 4 shows illustrative histograms in accordance with the present invention.

BEST MODE OF CARRYING OUT THE INVENTION

Reference is had to U.S. applicaton Ser. No. 939,943 of W. P. Hansen, assigned to the assignee hereof, filed Sept. 6, 1978, and entitled "APPARATUS AND METHOD FOR DETECTING PLATELETS IN WHOLE BLOOD". That application describes in detail a system suitable for application of the principles of the present invention. To the extent necessary to complete the instant disclosure, that application is incorporated by reference herein.

Figure 1:
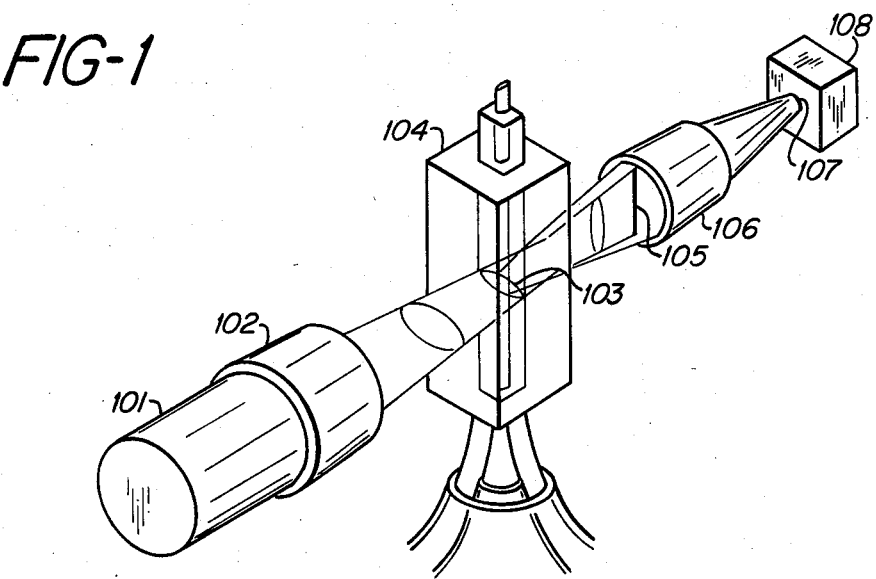
FIG. 1 shows a schematic diagram of a prior art system with which the principles of the present invention may be practiced.

Reference is also made to FIG. 1 hereof, which shows a relevant portion of the system disclosed by Hansen, which in conventional parlance incorporates the principles of dark field microscopy. In turn, these principles are employed to advantage in the aforementioned Ortho ELT-8 brand flow cytometry instrument. In the ensuing discussions, preferred embodiments of the present invention are discussed in the context of such an instrument, but it is to be understood that the principles of the present invention may be employed to equal advantage in any of the numerous commercially available cell counting and cell analysis systems which provide operation for which the present methods are appropriate.

In FIG. 1, a source of illumination 101 is focused by lens apparatus 102 onto a zone 103 in a flow cell 104. The flow cell 104 is oriented transversely to the focused illumination. In standard practice, hydrodynamic focusing insures that cells of a sample are marched rapidly individually through the zone, and are individually rapidly illuminated. It is highly desirable but not absolutely necessary that the dimension of the zone 103 in the direction of flow be generally smaller than the dimension of the cells in the flow direction. In the normal course, the illuminating intensity in the zone has a Gaussian distribution.

Light is scattered by the cell in all directions, but the narrow angle scatter suffices for the present invention. That light is collected after passing obstruction 105, optics 106, and through an aperture 107, at a detector 108. In practice, the detector 108 includes photoelectric means for developing an intensity (i.e., voltage) versus time depiction of the passing cell. See FIG. 2 which illustrates such waveforms.

As used herein, pulse width shall refer to the width, or time, between that time at which the pulse first reaches 50% of peak, to that time at which it drops below 50% of peak. Clearly, alternative definitions may be employed, but the 50%-50% definition is employed in preferred embodiments of the present invention.

Figure 2:
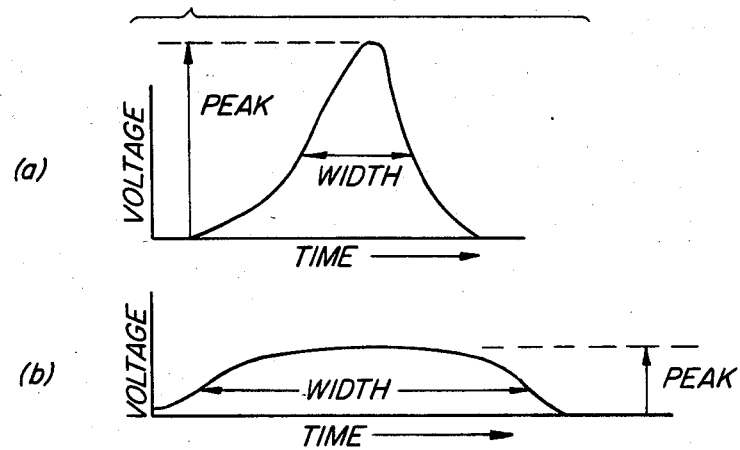
FIG. 2 shows an exemplary voltage pulse waveform of the narrow angle light scatter in the FIG. 1 system.

In preferred embodiments of the present invention, no changes to the ELT-8 optics are made. Additional electronics well within the capability of those of ordinary skill, may be used to analyze the red blood cell pulse shapes and to create pulse width and pulse shape histograms on the ELT-8 data handler. Alternatively, computer software embodying FIG. 3 hereof will properly analyze pulse width and pulse shape histograms as well as provide new information from the RBC histogram of pulse area previously displayed on the ELT-8. Although various factors can influence the RBC pulse width, pulse area and overall pulse shape, the primary cell features that relate to these parameters, as shown in FIG. 2, are thought to be:

| Pulse Parameter | Cell Feature |
| --- | --- |
| $P_A$ = Integrated area | Volume |
| $P_W$ = Width | Length or diameter |
| $P_S$ = Shape | Cell's gross shape |

In accordance with the principles of the present invention, cell morphology, or shape, is developed utilizing both a shape sensitive parameter and a shape insensitive parameter, on a cell by cell basis. Preferably, the ratio of pulse width (itself a function of time of flight) to pulse peak, provides such an indicium of pulse shape. Other combinations may, however, be employed, for example the ratio of pulse rise slope (e.g., the upswing time between 50% and 90% of peak) to pulse area or peak, or the ratio of pulse width to pulse area.

In the ELT analyzers, cells flow through a focused laser beam. The dimension of the beam in the direction of cell flow is approximately 7 $\mu$m, which is smaller than most red blood cells. The light intensity in the beam is not uniform, but rather is peaked in the center and falls off in a Gaussian distribution. As cells pass through this focused strip of laser light, they are in effect scanned by the laser beam. Since all cells flow at substantially the same speed in the fluid, a short cell spends a short time passing through the laser beam, and a longer cell spends a longer time in the laser beam. This time spent in the laser beam is reflected in the width of the light scatter pulse. See FIG. 2. Since cells tend to flow with their longest axis parallel to the direction of flow, the pulse width is a measure of the length of the longest dimension of a cell. If a cell is compact (e.g., spherical), it produces a taller, narrower pulse as in FIG. 2a. If the cell is longer and thinner, a shorter, wider pulse is produced as in FIG. 2b. The ratio of the width of the pulse to the peak height of the pulse is a good measure of the gross shape of the cell. The integrated area under the pulse is a good measure of cell volume, and is relatively independent of cell shape. In a normal individual, red blood cells have a well defined biconcave shape and a narrow range of sizes. The presence of significant numbers of cells with other than biconcave shape (e.g., spherical, spiked spherical, elongated, and sickle-shaped) is a condition referred to as poikilocytosis. If a wide range of cell sizes is present, the condition is known as anisocytosis. The presence of significant poikilocytosis or anisocytosis is often indicative of disease, and blood films are examined for these conditions during the "differential white cell count."

As used herein, the term "histogram" shall have the following meaning. A histogram is a plot or graph of the value of a parameter versus the number of occurrences of events with particular values of the parameter. The horizontal axis of the graph is divided into a number of equally sized and equally spaced segments or channels. Each segment or channel represents a particular range for the value of the parameter. The vertical axis of the graph represents the number of occurrences of events with each particular range of parameter values. Usually a continuous range of values, say 0 to 100, is divided into equal sized segments. FIG. 4 shows examples of histograms.

By analyzing the pulse area, pulse width, and pulse shape histograms, an index can be derived which indicates whether or not a blood sample contains significant numbers of abnormally shaped or sized red blood cells. Since small numbers of very abnormal cells may affect the pulse parameter histograms in a way similar to the effect of large numbers of less abnormal cells, the red cell abnormality or morphology index ("RCMI") in accordance with the present invention will not necessarily correlate numerically with the percentages of abnormal cells found in a manual morphological evaluation of a blood smear. There are also distinct differences in the condition of red cells evaluated in the ELT-8, in which cells are suspended in saline during evaluation, as compared with the manual evaluation, in which cells are dried onto a glass slide and fixed with alcohol. There is, nonetheless, a good correspondence between an elevated RCMI and the presence of significant numbers of abnormal red cells. That is, it is to be restated that the present methods provide a screen which may quickly be done without substantial intervention or exercise of judgment on a cell by cell basis. In the end, there is produced an index RCMI which will be subject to interpretation, that is, comparison with developed RCMI standards which indicate the relative desirability of proceeding with manual investigations.

As utilized herein, the term "coefficient of variation" shall be defined as:

$$CV = \frac{\sqrt{\Sigma n_i(S_i - \bar{S})^2}}{\bar{S}\sqrt{N}}$$

Where
i represents a channel in the histogram
$n_i$ is the number of counts in channel i
$S_i$ is the value of the abscissa variable s for that channel
$\bar{S}$ is the mean channel
$N = \Sigma n_i$ = total number of counts in the histogram Four distinct parameters are utilized in the calculation of the RCMI in accordance with the present invention. They are: (1) coefficient of variation of the major peak in the pulse width histogram; (2) coefficient of variation of the major peak in the pulse area histogram; (3) mean of the major peak in the pulse shape histogram, and (4) the coefficient of variation of the major peak in the pulse shape histogram. For each of these four parameters, the instrument is calibrated by analyzing normal blood samples, preferably on the ELT-8, and determining the mean and standard deviation of each parameter for normal blood samples.

The RCMI is computed as follows. The value of a parameter is compared with the normal value for that parameter. If the parameter is less than two normal standard deviations from the normal mean, no value is assigned the RCMI from the parameter. If the parameter is more than two normal standard deviations away from the normal mean, a value is assigned as $$RCMI(i) = \frac{|\text{Value of Parameter}(i) - \text{Mean Normal Value of Parameter}|}{\text{Normal Standard Deviation of Parameter}(i)} - 2$$

Note that the "−2" term results from adoption of the $2\sigma$ deviation criteria. Clearly, different statistical criteria will result in comparable variation of the foregoing algorithm.

Once the individual RCMI(i) parameters are so developed, it is only necessary to combine them. Generally, $$RCMI = A \cdot |RCMI(1)| + B \cdot |RCMI(2)| + C \cdot |RCMI(3)| + D \cdot |RCMI(4)|$$

where A, B, C, and D are weighting factors. In the simplest case, which also is the best mode contemplated at filing hereof, $$A = B = C = D = 1$$

Figure 3A:
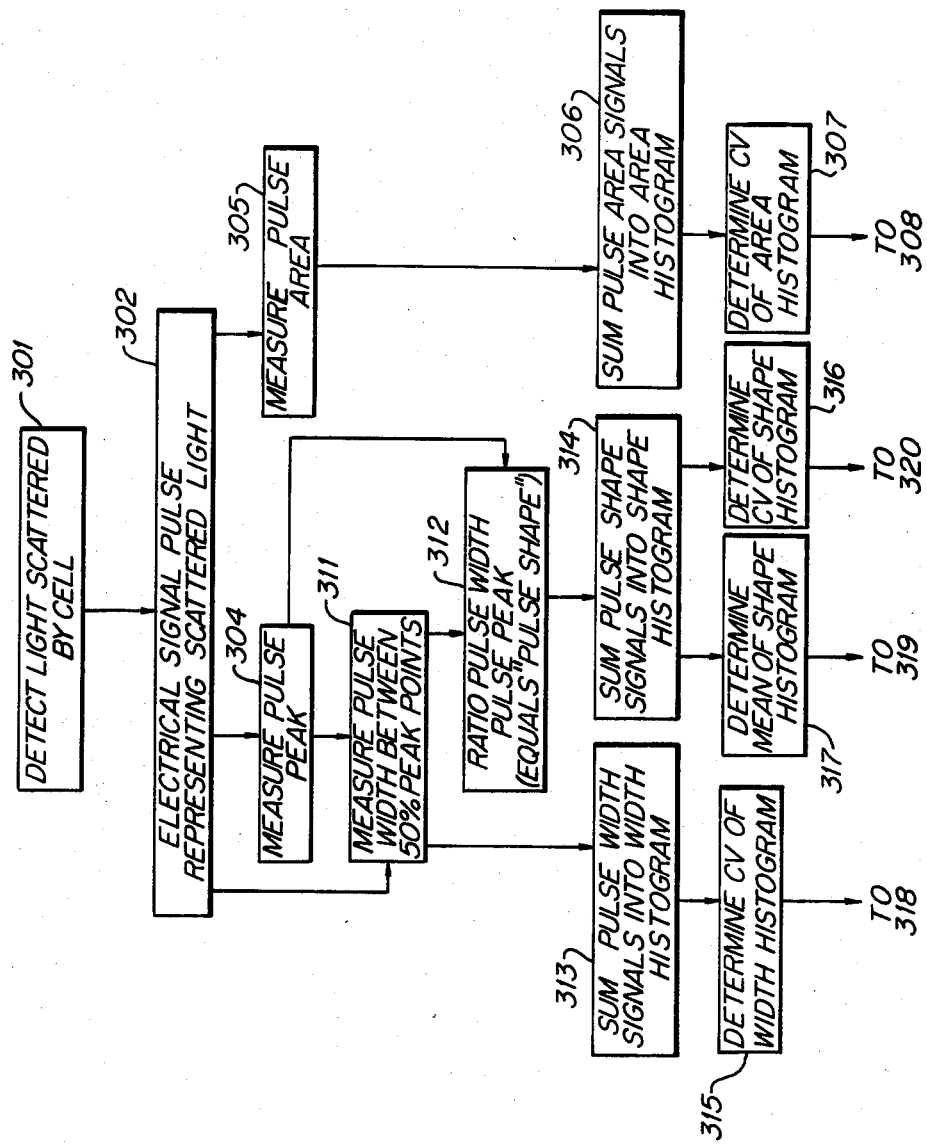

No doubt, the foregoing method will be better appreciated upon consideration of FIG. 3 which shows in flow chart form a preferred embodiment of the methods of the present invention. At 301, as the cell passes through the zone, scattered light is detected and a representative signal pulse is produced at step 302. Thereupon, parallel processes are conducted, one for pulse peak measurement, at 304, and one for pulse area measurement, as by integration, at step 305.

Considering first the area leg in its entirety, the respective values, cell after cell, are summed at 306 and collected in the form of a histogram. In turn, this histogram is analyzed at step 307, to determine the coefficient of variation, the area-sensitive parameter utilized for RCMI evaluation. Hence, at decision step 308, the area-CV is evaluated relative to a "normal" range, and if it is, pre-selected (i.e. the "yes" exit 309), no further computation will include the area-cv.

Understanding that the area-cv computation and the normality evaluation decision are "bulk" determinations, and that the individual legs in FIG. 3 are parallel operations, it is appropriate next to consider the "peak" leg of the procedure. Once the pulse peak is determined at 304, width between the ½ peak points may also be evaluated, and is done so for each cell, as represented by step 311. Likewise, then the pulse shape, or ratio of pulse width to pulse peak, may be calculated at step 312. Accordingly, data collection results in separate pulse width and pulse shape histograms, at steps 313 and 314, respectively. As noted, the coefficients of variation of the pulse width and shape histograms are evaluated in bulk at steps 315 and 316, respectively. Determination of the mean of the pulse shape histogram at step 317 provides the fourth morphology or abnormality criterion.

At respective decision steps 318, 319, and 320, the width-cv, shape mean, and shape-cv values are compared with predetermined ranges designated "normal" for each. As is the case of the area-cv, previously discussed, occurrence within range results in exit via the "yes" leg, and no further dispositive action.

If any or all of the decision steps 308, 318, 319, or 320 exit via the "No" leg, indicating a value outside the designated "Normal" range, there results a computation of the RCMI factors. In fact, the "Normal" decision corresponds to the $2\sigma$ computation of RCMI(i) previously discussed for preferred embodiments. The RCMI compute step 321 is the calculation of the total RCMI index.

Thus, at step 322, the developed RCMI may be evaluated relative to a preset threshold: if above the threshold, further study conventionally through manual methods will be required, but if not, that laborious process is obviated.

FIG. 4 illustrates three histograms produced in accordance with steps 313, 314, and 306 of FIG. 3. Each may thereupon be processed for suitable data required. That is, coefficient of variation for all three, and mean for the pulse shape histogram, result therefrom.

Figure 5:
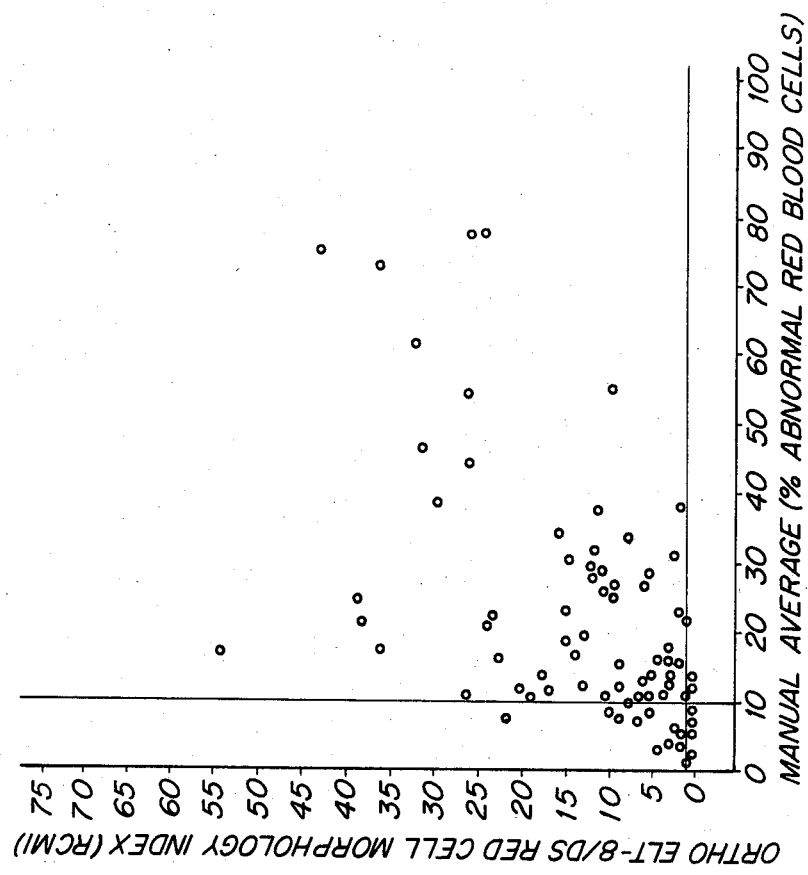
FIG. 5 shows a chart of comparison of the present invention with manual methods common in the art.

FIG. 5 illustrates actual data correlation of the principles of the present invention with prior art manual techniques. In FIG. 5, RCMI is plotted on the ordinate, and the manual evaluation is plotted on the abscissa.

For purposes of analysis of FIG. 5, let it be assumed that the manual index of abnormality is 10%, a realistic number, and that the RCMI index of 1 or greater indicates a degree of morphology worthy of detailed investigation (i.e., the "yes" exit of step 322 in FIG. 3). The truth table of FIG. 5 demonstrates the correspondence and significance of the data set forth on the FIG. 5 graph.

It will be appreciated from the foregoing that the principles of the present invention embrace various techniques for making automated decisions regarding morphology. Numerous variations and adaptations will occur to those of ordinary skill in the art without departure from the spirit or scope of the principles of the present invention.

We claim:

1. In an optical cell analysis system, a method for screening cells from a sample of cells for red blood cell abnormalities comprising the steps of:

(a) passing the cells of said sample, one at a time in sequence, through a zone of focused illumination, (b) for each of said cells, developing a pulse waveform representative of predetermined light scatter from said zone;

(c) developing respective data collections, based on given samples of cells, of pulse widths and pulse areas;

(d) developing, for each cell, as an indicium of pulse shape, the ratio of pulse width to pulse peak, and developing a collection of pulse shape indicia;

(e) computing respective coefficients of variation, of said pulse width, pulse area, and pulse shape indicia collections;

(f) combining said coefficients of variation in accordance with a predetermined function, thereby producing a red cell abnormality index;

(g) evaluating said red cell abnormality index relative to predetermined standards to identify samples having significant degrees of red cell abnormality.

2. A method as described in claim 1 wherein said step of combining further comprises identifying the mean of said collection of pulse shape indicia, and combining it with said coefficients of variation.

3. A method as described in claim 2 wherein said step of combining coefficients of variation comprises first developing an index of abnormality for each said coefficient, and then for combining those individual indices which fall outside a select range of acceptability.

* * * * *